US00PP08045P

United States Patent [19]

van der Knaap

[11] Patent Number: Plant 8,045

[45] Date of Patent: Nov. 24, 1992

[54] CHRYSANTHEMUM PLANT — YELLOW IMPALA CULTIVAR

[75] Inventor: Jacques C. M. van der Knaap, DeLier, Netherlands

[73] Assignee: Fides Beheer B.V., De Lier, Netherlands

[21] Appl. No.: 679,536

[22] Filed: Apr. 2, 1991

[51] Int. Cl.[5] ..... A01H 5/00

[52] U.S. Cl. ..... Plt./82.2

[58] Field of Search ..... Plt./74, 74.1, 82.1, Plt./82.2

*Primary Examiner*—Howard J. Locker

*Attorney, Agent, or Firm*—Burns, Doane, Swecker & Mathis

[57] ABSTRACT

A new and distinct cultivar of Chrysanthemum plant named Yellow Impala is provided. The new cultivar is a spontaneous mutation of the Cream Impala cultivar (non-patented in the United States). More specifically, the new cultivar forms attractive yellow single flowers having a yellow-green center when immature. The response period of the flowers is approximately nine weeks. The new cultivar is particularly suited for use in the production of a cut single spray under greenhouse conditions.

1 Drawing Sheet

SUMMARY OF THE INVENTION

The present invention comprises a new and distinct cultivar of Chrysanthemum, botanically known as *Dendranthema morifolium* Ramat., previously, *Chrysanthemum morifolium,* Ramat., and hereinafter is referred to by the cultivar name Yellow Impala.

The new cultivar is a spontaneous mutation of unknown causation which was discovered and carefully preserved during July, 1986 during the course of plant selection work which was conducted by me. The new cultivar was discovered among plants of the Cream Impala cultivar (U.S. Plant Pat. No. 6,743) being grown under my direct supervision at De Lier, The Netherlands, which formed blossoms having ray florets possessing the characteristic cream coloration. The Cream Impala cultivar parent was a mutation of the Impala cultivar (U.S. Plant Pat. No. 6,095) which forms blossoms having ray florets possessing the characteristic pink coloration.

It was observed that a single plant consistently formed flowers having ray florets of a distinctive yellow coloration. All other characteristics of this plant were found to be substantially identical to those of the Cream Impala and Impala cultivars. Had I not discovered, carefully studied, and preserved this new cultivar it would have been lost to mankind. This new cultivar is particularly well suited for growing in the production of a cut single spray.

It was found that the new cultivar of the present invention:

(a) exhibits attractive yellow single flowers having an overall diameter of approximately 70 to 80 mm. wherein the disc florets are yellow-green in coloration when immature,
(b) exhibits a flower response period of approximately nine weeks, and
(c) has the ability to produce flowers of commercially acceptable quality throughout the year in a cut mum production program.

Asexual reproduction of the new cultivar by cuttings as performed at De Lier, The Netherlands, in a controlled environment has demonstrated that the characteristics of the new cultivar as herein disclosed are firmly fixed and are retained through successive generations of asexual propagation.

Yellow Impala has not been observed under all possible environmental conditions to date. Accordingly, it is possible that the phenotype may vary somewhat with variations in the environment, such as temperature, light, day length, contact with pesticides and/or subjection to growth retardant treatments.

When the new cultivar of the present invention is compared to the Impala cultivar (U.S. Plant Pat. No. 6,095) and the Yellow Impala cultivar (non-patented in the United States), it is found to exhibit a distinctive yellow ray floret coloration unlike the pink ray floret coloration of Impala and the cream ray floret coloration of Cream Impala. Otherwise, the overall vigor, foliage appearance, and flower type tend to be substantially the same in each instance.

BRIEF DESCRIPTION OF THE PHOTOGRAPH

The accompanying photograph shows as nearly true as it is reasonably possible to make the same in a color illustration of this character, a typical specimen of an overall plant of the new cultivar. The plant was grown in a greenhouse at De Lier, The Netherlands.

DETAILED DESCRIPTION

The chart used in the identification of colors described hereafter in The R.H.S. Colour Chart of The Royal Horticultural Society, London, England. The color values were determined at 11:00 a.m. to 12:00 noon under natural daylight conditions at De Lier, The Netherlands, during October, 1987. The plants described were grown under standard greenhouse conditions which approximate those commonly utilized for the production of cut mums.

Classification:

*Botanical.*—*Dendranthema morifolium* Ramat., cv. Yellow Impala.

*Commercial.*—Cut single spray.

Inflorescence

A. Capitulum:

*Form.*—Flat.

*Type.*—Single or Daisy.

*Diameter across face.*—Approximately 70 to 80 mm. on average.

*Diameter of disc.*—Approximately 15 to 20 mm. on average.

B. Corolla of ray and disc florets:

*Color (General tonality from a distance of three meters).*—Yellow.

*Color ray florets.*—(Top surface). — Yellow Group 9A. (Under surface). — Yellow Group 9C.

*Color disc florets.*—Yellow-Green Group 144C when immature.

C. Reproductive organs:

*Androecium.*—Present in disc florets.

*Gynoecium.*—Present in both disc and ray florets.

Plant

A. General appearance:

*Height.*—Approximately 90 cm. on average.

B. Foliage:

*Color (upper surface).*—Yellow-Green Group 147A.

*Shape.*—Long lobed and deeply serrated.

I claim:

1. A new and distinct cultivar of Chrysanthemum plant named Yellow Impala, substantially as herein shown and described, which:

(a) exhibits attractive yellow single flowers having an overall diameter of 70 to 80 mm. wherein the disc florets are yellow-green in coloration when immature, (b) exhibits a flower response period of approximately nine weeks, and (c) has the ability to produce flowers of commercially acceptable quality throughout the year in a cut mum production program.

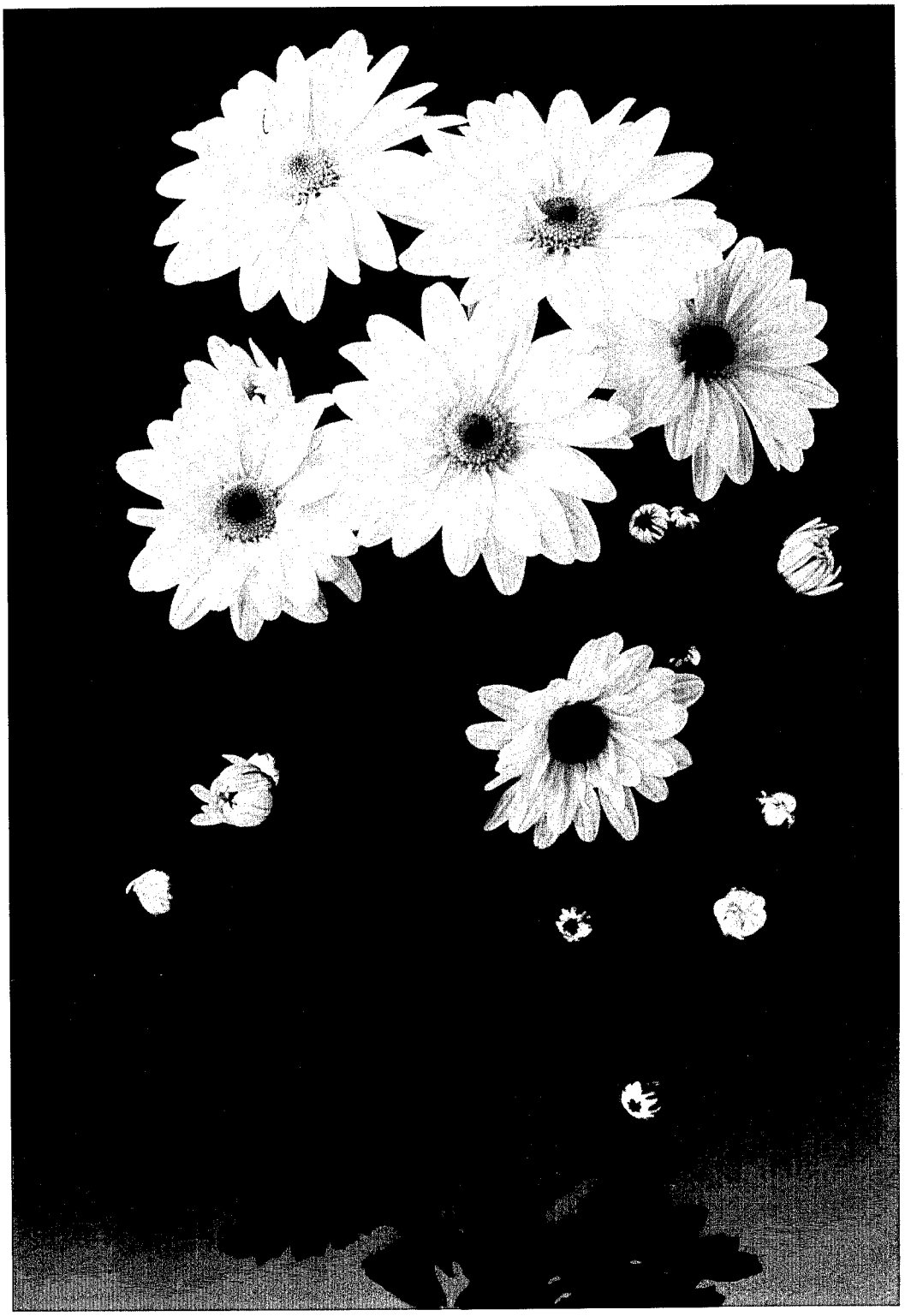

* * * * *